(12) United States Patent
Bordoloi et al.

(10) Patent No.: US 10,188,599 B2
(45) Date of Patent: Jan. 29, 2019

(54) ANTI-INFLAMMATORY ACTIVITY WITH SYNERGISM OF HERBAL ESSENTIAL OILS

(71) Applicant: Bordoloi Biotec, LLC, Bridgewater, NJ (US)

(72) Inventors: Binoy K Bordoloi, Bridgewater, NJ (US); Kulwant S Saini, Gurgaon (IN)

(73) Assignee: BORDOLOI BIOTECH, LLC, Bridgewater, NJ (US)

( * ) Notice: Subject to any disclaimer, the term of this patent is extended or adjusted under 35 U.S.C. 154(b) by 0 days.

(21) Appl. No.: 15/685,209

(22) Filed: Aug. 24, 2017

(65) Prior Publication Data

US 2018/0078494 A1 Mar. 22, 2018

(30) Foreign Application Priority Data

Sep. 17, 2016 (IN) .............................. 201631031742

(51) Int. Cl.
| | | |
|---|---|---|
| *A61K 9/00* | (2006.01) | |
| *A61K 9/107* | (2006.01) | |
| *A61K 9/06* | (2006.01) | |
| *A61K 36/906* | (2006.01) | |
| *A61K 36/758* | (2006.01) | |
| *A61K 36/899* | (2006.01) | |
| *A61K 47/44* | (2017.01) | |

(52) U.S. Cl.
CPC ............ *A61K 9/0014* (2013.01); *A61K 9/06* (2013.01); *A61K 9/107* (2013.01); *A61K 36/758* (2013.01); *A61K 36/899* (2013.01); *A61K 36/906* (2013.01); *A61K 47/44* (2013.01)

(58) Field of Classification Search
CPC combination set(s) only.
See application file for complete search history.

(56) References Cited

U.S. PATENT DOCUMENTS

| 7,368,135 B1 * | 5/2008 | Anderson | A61K 36/00 424/725 |
|---|---|---|---|
| 7,838,045 B2 | 11/2010 | Ribnicky et al. | |
| 7,871,647 B1 | 1/2011 | Paradise | |

FOREIGN PATENT DOCUMENTS

WO  2015000064 A1  1/2015

OTHER PUBLICATIONS

Garcia et al., "Evaluation of Anti-inflammatory and Analgesic Activities of Cymbopogon citratus in vivo-Polyphenols Contribution," Research Journal of Medicinal Plant 9 (1): 1-13, 2015. (Year: 2015).*

Ibrar et al., "Antinociceptive and anticonvulsant activities of essential oils of Zanthoxylum armatum," Phytopharmacology 2012, 3(1) 191-198. (Year: 2012).*

Tandan et al., "Analgesic and Anti-inflammatory Effects of Hedychium spicatum," Indian Journal of Pharmaceutical Sciences, May-Jun. 1997, 148-150. (Year: 1997).*

(Continued)

*Primary Examiner* — Aradhana Sasan
(74) *Attorney, Agent, or Firm* — Dave Law Group LLC; Raju Dave

(57) ABSTRACT

The present invention relates to a topical synergistic anti-inflammatory formulation comprising a blend 1 to 6% by weight of *Cymbopogon citratus* oil (CC oil); 0.5 to 6% by weight of *Zanthoxylum armatum* oil (ZA oil); 0.5 to 6% in weight by *Hedychium spicatum* oil (HS oil). The invention also provides a method of management of the pain and/or inflammation by the formulations of the invention.

19 Claims, 4 Drawing Sheets

(56) References Cited

OTHER PUBLICATIONS

Giri, D. et al. "A review account on medicinal value of Hedychim spicatum Buch-Ham ex Sm: Vulnerable medicinal plant" J. Med. Plants Res., 4(25), 2773-2777, 2010.
Mitoshi et al. "Suppression of Allergic and inflammatory responses by essential oil derived from herbal plants and citrus fruits" Int. J.Mol.Med. 33:1643-1651, 2014.
Singh, T.P. and Singh, O.M. "Phytochemical and prarmalogical profile of Zanthoxylum armatum DC.—An overview" Ind. J. Nat. Prod. Res. 2(3), 275-295, 2011.

\* cited by examiner

ANTI-INFLAMMATORY ACTIVITY WITH SYNERGISM OF HERBAL ESSENTIAL OILS

CROSS-REFERENCE TO RELATED APPLICATIONS

This disclosure claims the benefit of priority to Indian Patent Application No. 201631031742, filed Sep. 17, 2016, the disclosure of which is incorporated herein in its entirety.

FIELD OF THE INVENTION

The present invention relates to formulation for reducing the symptoms of inflammation in connective tissue of joints and muscles resulting in pain. More particularly, the present invention relates to formulations comprising the synergistic combination of three essential oils, which exhibit significantly enhanced anti-inflammatory activity with reduced side effects.

BACKGROUND

Arthritis is a disease due to the inflammation of connective tissue in joints, resulting in pain, swelling, stiffness and loss of function of the joints. The most common types of arthritis are osteoarthritis (OA) and rheumatoid arthritis (RA). Biologics based injections are the leading drugs for RA. For example, brands like Humira, Enbrel and Remicade accounted for 2015 sales exceeding $30 billion. Although effective, these drugs are expensive and are known to have certain side effects, which requires continuous medical attention of a physician. In general, these drugs block a protein called tumor necrosis factor (TNF), that's involved in inflammation. Therefore these drugs are often called anti-TNF or TNF inhibitors. Similarly, Rumalaya forte of the Himalaya Drug Company, India is an oral dose medication that is reported to act as a TNF inhibitor. It is reported to be effective for both OA and RA, though it is not expected to be as effective as the biologic drugs.

OA is a chronic condition occurring more frequently as people get older and can break down joint's protective cartilage causing damage and pain. OA pain develops slowly and may require daily management for pain. While there is no known cure for OA, there are treatments that can help one relieve the pain in the joints. Physicians recommend the use of topical non-steroidal anti-inflammatory drugs (NSAIDs) for OA joint pain, at a lowest possible dose of medication for the shortest time to achieve pain relief. Voltaren Gel is one such available NSAID, used for the relief of joint pain of OA in the knee, ankles, feet, elbows, wrists and hands. It is applied on clean, dry skin that does not have any cuts, infections, or rashes. However, it is recommended that one should not use the gel along with any oral NSAIDs.

Doctors have long treated auto-immune diseases such as arthritis as a case of confused immune system. Here immune cells appear to decide that healthy tissue looks foreign and wage an attack. If the immune system is not actually confused but it is reacting to normal molecules that wound up in an abnormal place, the mechanism of action would be different. Padlock Therapeutics, USA thinks that the right way could be to block those errant molecules rather than blocking the immune system itself. This contrarian view of autoimmunity is based on evidence around a family of enzymes called protein arginine deiminases (PADs). Under normal conditions PADs live inside cells. But if they escape, immune cells start action, and a series of events begin to take place including what's known as protein citrullination, which is linked to RA. Padlock is designing small molecules to block this PAD activity.

Thus, techniques for managing OA and RA are based on man-made either biological large molecules or synthetic small molecules, however, there are medications also derived from plant extracts. These extracts are a mixture of several smaller molecules of varying chemistries. For example, Topricin is such a topical homeopathic cream to treat foot and ankle pain for neuropathy. Here the plant extract is a vasodilator, to treat the pain in the limbs relating to restricted blood flow to nerve endings and reduction in motor and sensory nerve conduction velocities.

Thus, a range of synthetic NSAIDs based formulations is available, which produce their own side effects based on the amount of active ingredient and duration of therapy. On the contrary, herbal formulations are also available which although are effective, but do not exhibit an effect that is higher or equivalent to the NSAIDs based topical formulations.

U.S. Pat. No. 7,871,647 discloses a composition for treating fibromyalgia pain consisting essentially of *Aesculus hippocastanum* extract, *Arnica montana* extract, L-arginine, *Echinacea augustfolia* extract, *Rhus toxicondendron* extract, *Ruta graveoleus* extract, graphites, *Crotalus horridus* extract, *Heloderma horridum* extract, *Lachesis* extract, *Naja* extract, isopropyl myristate, and capsaicin for homeopathic treatment.

U.S. Pat. No. 7,838,045 discloses an anti-inflammatory formulation of *Barbarea verna* seed containing phenethyl-isothiocyanate, which can be used for treatment of many inflammation-related conditions, including but not limited to rheumatoid and osteoarthritis, acute and chronic pains, lupus, irritable bowel disease, cancer and metabolic syndrome.

Mitoshi et. al. in *International Journal of Molecular Medicine*, 33, 1643-1651, 2014, published a study on the biological activity of twenty essential oils (EOs). The publication discloses Lemon Grass (*Cymbopogon citratus* oil or CC oil) to elicit strong anti-inflammatory and anti-allergic effects. The activity was determined by measuring the TNF-alpha in murine macrophage. Further, the principal component of CC oil was reported to be Citral.

Council for Scientific and Industrial Research and Northeast Institute of Science and Technology, India provides a topical ointment based on a blend of EOs of 2% *Eucalyptus globulus* oil, 2% *Cinnamomum tamala* oil, 2% *Zanthoxylum armatum* oil and 1% *Hedychium spicatum* oil for the treatment of OA and RA. The said gel based ointment was studied on both arthritic mice model and human clinical RA patients for effect on levels of cytokines.

D. Giri et al, in *Journal of Medicinal Plants Research*, Vol. 4(25), pp. 2773-2777, 2010 discloses the anti-inflammatory activity of *Hedychium spicatum*.

WO 2015000064 discloses a composition to treat pain and/or inflammation comprising beta-caryophyllene or a functionally equivalent derivative, analogue or pharmaceutically acceptable salt thereof, and eugenol or a functionally equivalent derivative, analogue or pharmaceutically acceptable salt thereof. It discloses beta-caryophyllen derived from *Zanthoxylum armatum*.

However, there remains a need to develop new and alternative anti-inflammatory formulations having enhanced synergistic anti-inflammatory effect. It is also desirable that such formulations have minimal or no side effects thus being safe to administer. More specifically, there is a need to develop a topical formulation which provides an enhanced anti-inflammatory effect with a high benefit to low risk ratio.

SUMMARY

In one aspect of the present invention there is provided a topical synergistic anti-inflammatory formulation comprising a blend of 1 to 6% by weight of *Cymbopogon citratus* oil (CC oil); 0.5 to 6% by weight of *Zanthoxylum armatum* oil (ZA oil); 0.5 to 6% by weight of *Hedychium spicatum* oil (HS oil).

In another aspect of the present invention there is provided a topical synergistic anti-inflammatory formulation comprising a blend of 1 to 6% by weight of *Cymbopogon citratus* oil (CC oil); 0.5 to 6% by weight of *Zanthoxylum armatum* oil (ZA oil); 0.5 to 6% by weight of *Hedychium spicatum* oil (HS oil) wherein the weight proportion of CC oil, ZA oil, and HS oil is 60%, 20% and 20% respectively.

In a further aspect of the invention there is provided a method of management of pain and/or inflammation in a mammal, said method comprising administering at the site of pain and/or inflammation a formulation comprising a blend of 1 to 6% by weight of *Cymbopogon citratus* oil (CC oil); 0.5 to 6% by weight of *Zanthoxylum armatum* oil (ZA oil); 0.5 to 6% by weight of *Hedychium spicatum* oil (HS oil).

In a yet another aspect of the invention there is provided a method of management of pain and/or inflammation in a mammal, said method comprising administering at the site of pain and/or inflammation a formulation comprising a blend of 1 to 6% by weight of *Cymbopogon citratus* oil (CC oil); 0.5 to 6% by weight of *Zanthoxylum armatum* oil (ZA oil); 0.5 to 6% by weight of *Hedychium spicatum* oil (HS oil); and wherein the weight proportion of CC oil, ZA oil, and HS oil is 60%, 20% and 20% respectively.

BRIEF DESCRIPTION OF THE FIGURES

For a more complete understanding of the disclosure, reference should be made to the following detailed description and accompanying drawing figures wherein.

DETAILED DESCRIPTION

Figure 1:
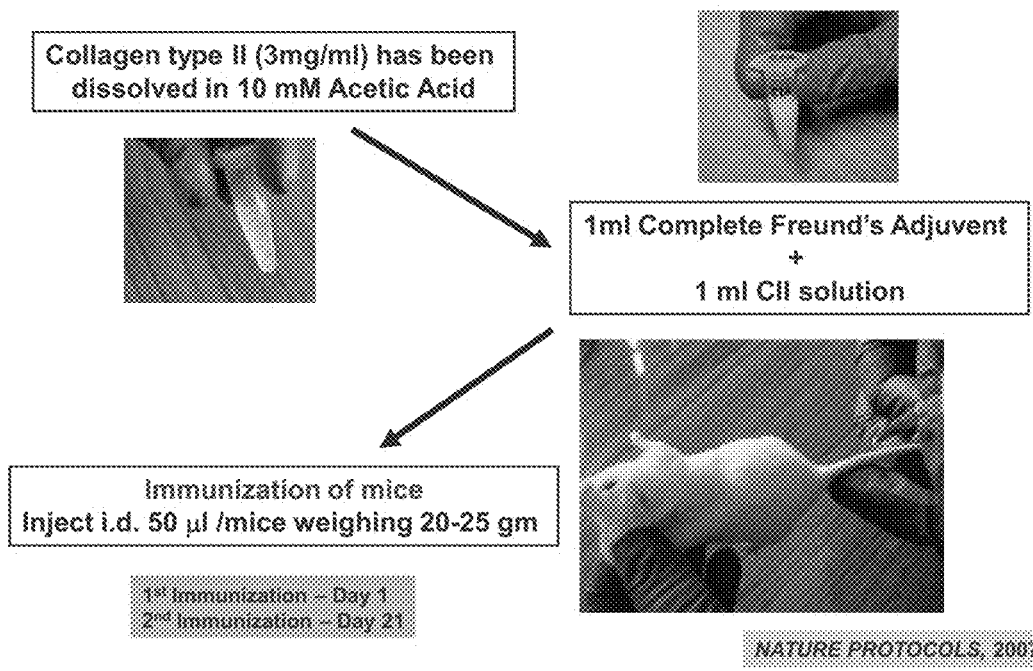
FIG. 1 is a graphical representation of the method for collagen induced arthritis mice model.

It is an object of the invention to overcome the drawback of the prior art.

It is another object of the invention to provide a synergistic herbal formulation comprising *Cymbopogon citratus* oil [also known as Lemon Grass oil or CC oil], *Zanthoxylum armatum* oil (ZA oil), and *Hydachium spicatum* oil (HS oil).

It is another object of the invention to provide a topical formulation that has potential anti-inflammatory activity for symptoms such as frozen shoulder, stiff neck, backaches, musculoskeletal pains and rheumatoid arthritis, osteoarthritis, cervical and ankylosing spondylitis and sciatica.

It is yet another object of the invention to provide formulations as aforesaid that act without exerting toxic or side effects.

It is still another object of the invention to provide synergistic herbal formulations that provides relief of minor aches and pain of muscle and joints in arthritis.

It is a further object of the invention to provide a method of management of pain and/or inflammation in a mammal with minimal toxic or side effects.

The present invention relates to anti-inflammatory and analgesic formulation for management of inflammation disorder selected from the group consisting of rheumatoid arthritis, osteoarthritis, inflammatory bowel disease, Crohn's disease, ulcerative colitis, multiple sclerosis, psoriasis, and skin rashes. This includes frozen shoulder, stiff neck, backaches, musculoskeletal pains and rheumatoid arthritis, osteoarthritis, cervical and ankylosing spondylitis and sciatica.

The present invention provides a topical herbal formulation that provides anti-inflammatory and/or analgesic effect without producing any major side effects even on prolonged use. The invention discloses a blend of essential oils comprising *Cymbopogon citratus* (CC oil), *Zanthoxylum armatum* oil (ZA), and *Hedychium spicatum* oil (HS), which exhibit enhanced anti-inflammatory and analgesic effect compared to the known formulations having the individual essential oils. The invention can further include an essential oil obtained from basil, caraway, carrot seed, celery seed, chamomile, citronella, clary sage, clove, cumin, lemon, marjoram, nutmeg, orange, sage, sandalwood, spearmint, and/or thyme. In another instance, the blend of essential oils includes at least three oils selected from (A) *Cymbopogon citratus* (CC oil), (B) *Zanthoxylum armatum* oil (ZA), (C) *Hedychium spicatum* oil (HS), and (D) an essential oil obtained from basil, caraway, carrot seed, celery seed, chamomile, citronella, clary sage, clove, cumin, lemon, marjoram, nutmeg, orange, sage, sandalwood, spearmint, and/or thyme.

In the present invention, a topical anti-inflammatory and/or analgesic formulation comprising a blend of essential oils, namely, *Cymbopogon citratus* oil, *Zanthoxylum armatum* oil, and *Hedychium spicatum* oil showing synergistic effect is disclosed.

In an embodiment, the topical anti-inflammatory and/or analgesic formulation comprises a blend of essential oils at about 2 to 16% by weight; wherein said blend comprises: *Cymbopogon citratus* oil at about 1 to 6% by weight; *Zanthoxylum armatum* oil at about 0.5 to 6% by weight; and *Hedychium spicatum* oil at about 0.5 to 6% by weight.

The present inventors surprisingly found that upon combining the essential oils in a certain ratio, the formulation demonstrated synergistic activity while being non-toxic and safe. The said formulation comprising a blend of *Cymbopogon citratus* oil, *Zanthoxylum armatum* oil and *Hedychium spicatum* oil in a weight proportion of 60%, 20% and 20% respectively. Herein, the weight proportion provides the ratio of the essential oils; a weight proportion of 60%, 20%, 20%, provides a mass ratio of 3:1:1.

The formulation of the present invention further comprises menthol, a pure herbal compound, which produces a cooling sensation and has analgesic properties. Preferably, Menthol, (CAS No. 2216-51-5) of USP grade, water-white crystal and characteristic odor is used. The concentration of menthol in the formulation may vary from 1 to 16% by weight. Preferably, the concentration is 1.3% by weight.

The formulation of the present invention may be made in the form of a cream, gel, lotion or a sprayable system. Preferably the formulation is in form of an emulsion. More preferably the formulation is in form of an aqueous cream for topical application.

The formulation of the present invention is found to manage the symptoms of disease associated inflammation which are measured by the high levels of inflammatory cytokines in blood serum. Experiments were conducted for establishing the said effects. The increased level pro-inflammatory cytokines, for example, TNF-alpha, Interleukin-1beta (IL-1beta) and Interleukin-6 (IL-6), were measured quantitatively in blood serum in a collagen induced arthritic mice model, and then compared with the effect after topical treatment with the present formulation, to establish the anti-inflammatory effect of the formulation.

The present inventors surprisingly observed that after topical treatment with the formulation of the present invention over a period of three weeks, the cytokine levels i.e. TNF-alpha, IL-6 and IL-1beta, showed a remarkable lowering, specifically to the extent of at least 50%.

Figure 2:
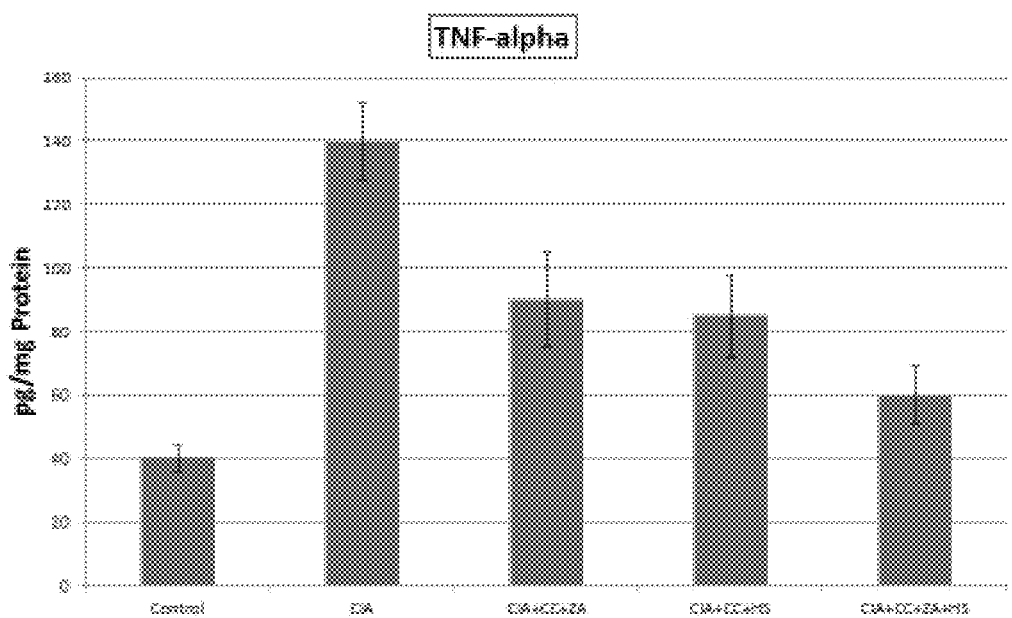
FIG. 2 is a graphical representation of Cytokine TNF-alpha Level in various systems of EOs, namely (a) CC+ZA at 60% and 40%, (b) CC+HS at 60% and 40%, and (c) CC+ZA+HS at 60%, 20% and 20% respectively.
Figure 3:
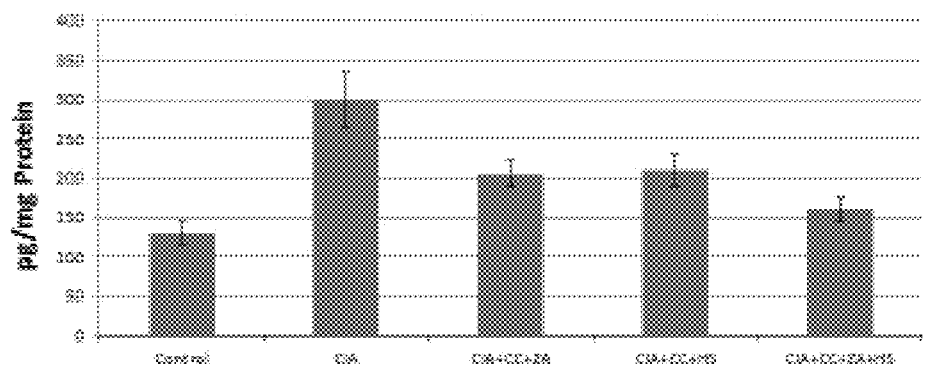
FIG. 3 is a graphical representation of Cytokine, IL-6 Level in various systems of EO's, namely (a) CC+ZA at 60% and 40%, (b) CC+HS at 60% and 40%, and (c) CC+ZA+HS at 60%, 20% and 20% respectively.
Figure 4:
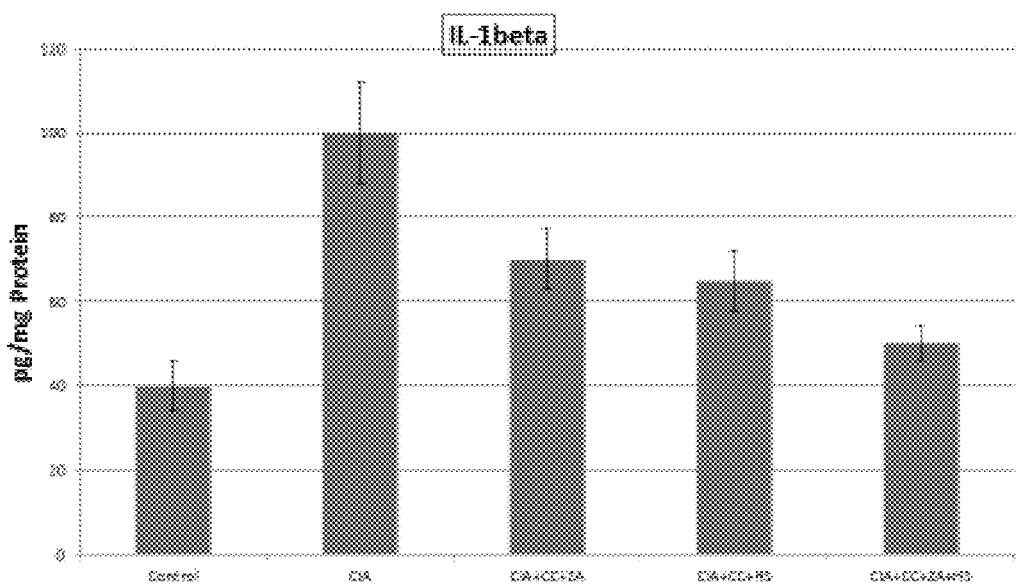
FIG. 4 is a graphical representation of Cytokine, IL-beta Level in various systems of EO's, namely (a) CC+ZA at 60% and 40%, (b) CC+HS at 60% and 40%, and (c) CC+ZA+HS at 60%, 20% and 20% respectively While specific embodiments are illustrated in the figures, with the understanding that the disclosure is intended to be illustrative, these embodiments are not intended to limit the invention described and illustrated herein.

As observed in FIGS. 2, 3 and 4 there is remarkable decrease in the Cytokine Levels on Arthritic Mice; Control Healthy Mice Before Collagen Injection (Con), Arthritic Mice After Collagen Injection (CIA), Arthritic Mice After 21 Days of Treatment with Three Systems of EO's, namely (a) CC+ZA at 60% and 40%, (b) CC+HS at 60% and 40%, and (c) CC+ZA+HS at 60%, 20% and 20% respectively. Examples 2, 3 and 4 show that CC as well as CC oil with either ZA oil or HS oil as blends showed a decline in TNF-alpha, IL-6 and IL-1beta. Surprisingly, CC oil with a combination of ZA oil and HS oil, while maintaining the same total weight % of ZA and HS, showed consistently and significantly higher decline of the cytokine levels, displaying synergism in an unexpected manner. Thus, also showing that the high anti-inflammatory effect is achieved while using less concentration of actives and thus reducing the toxic or side effects that may be produced on prolonged use.

As mentioned above the essential oils are formulated into various topical anti-inflammatory and/or analgesic formulations.

In another embodiment the formulation is provided as an oil-in-water type emulsion which includes a fine particles of the essential oils. The fine particle of essential oil includes an effective amount of *Cymbopogon citratus* oil, *Zanthoxylum armatum* oil, and *Hedychium spicatum* oil and the Menthol crystals, in an aqueous medium and at least one emulsifier for dispersing the fine particles of the essential oils in the aqueous medium. The oil-in-water emulsion may include inactive oil(s) for better oil-water balance and emulsification. Examples of such oils include jojoba oil, coconut oil, almond oil, *eucalyptus* oil and avocado oil. The oil-in-water emulsion includes a base, preferably triethanolamine.

The formulation of the present invention may further comprise one or more of the conventional optional components known for use in topical anti-inflammatory and/or analgesic formulations, provided that the components used are compatible with the essential oils and menthol components of the formulation both physically and chemically. These optional components should generally not impair the stability, aesthetics or performance of the product. Concentrations of such optional components typically range from about 0.001% to about 25% by weight of the formulation.

Such conventional optional ingredients are well known to those skilled in the art and may be selected from the group comprising but not restricted to emulsifiers, co-emulsifiers, rheology modifiers, solubilizers, preservatives such as sodium benzoate, benzyl alcohol, methyl paraben and propyl paraben; thickeners and viscosity modifiers; perfumes; dyes; pH adjusting agents etc.

The formulation thus formed is applied topically and is indicated for the management of arthritis associated symptoms of pain and inflammation and related conditions including but not limited to rheumatoid arthritis, osteoarthritis, inflammatory bowel disease, Crohn's disease, ulcerative colitis, multiple sclerosis, psoriasis and skin rashes and other related disorders for reducing the production of pro-inflammatory cytokines.

The emulsifiers and co-emulsifiers are present in formulations of the invention in an amount of from 1 to 3%±1% by weight. These may preferably include Phoenoxol T, as emulsifier and Glyceryl stearate as co-emulsifier.

In an embodiment, the process for making the aqueous cream with the said blend of EOs i.e. wherein the weight proportion of CC oil, ZA oil, and HS oil is 60%, 20% and 20% respectively, includes the following steps: In phase-A, preservative and thickener are mixed together while heating. In phase-B, Emulsifier and Co-emulsifier are mixed together and heated, followed by addition of the EOs blend, so as to ensure minimum heating of the blend of oils. In phase-C, menthol is solubilized by mixing with solubiliziers and then warming. In phase-D, a base mixture is prepared to neutralize the pH from the added thickener to the required pH (We still keep it slightly acidic as the skin pH is acidic). Thus, four separate phases A, B, C, D are prepared. Then the phase B of blend of EOs in emulsifier is added to Phase A with preservative at 65-70° C. while rotating at 400 to 500 rpm. To the prepared mixture, phase D with base is added, while raising the rotation speed. Later, the formed mixture of Phase ABD is cooled and then phase C with solubilized menthol is added, while mixing. This is cooled and then mixed with deionized water in q.s. to obtain the cream.

In another aspect is provided a method of managing pain and/or inflammation in a mammal. The method comprising administering at the site of pain and/or inflammation a formulation as described herein.

The terms "manage", "management", "treat", "treating" and "treatment" are used broadly herein to denote methods that moderate, ameliorate, reverse the progression of, reduce the severity of, or prevent pain and/or inflammation. In this regard it is noted that because a wide range of inter-individual variability exists in the perception of pain, the perceived result of the present treatment may vary from mammal to mammal.

In one embodiment, the method includes topical application of the formulation to a mammal in need of pain and/or inflammation treatment.

The formulation is preferably rubbed onto the skin to promote absorption of the active ingredients. The formulation is administered at a dosage suitable to manage pain and/or inflammation. The composition is generally applied one to three times a day by means of a light massage on the affected area for a period of time sufficient to treat pain and/or inflammation. The duration may vary depending on the severity and other factors. For more severe cases, however, the composition may be applied more frequently, e.g. three or more times a day for a period of time sufficient to treat the pain and/or inflammation.

EXAMPLES

The present invention is now demonstrated by way of illustrative non-limiting examples. Other variations as may be obvious to one skilled in the art may be made in compounds, formulations, and methods described herein without departing from the essential features of the invention. These and such others may be considered illustrative and non-restrictive to the scope of the present invention.

Example 1

The 3 EO's and menthol was procured from Katyani Exports, Delhi, India. These included:

*Cymbopogon citratus* oil, CC oil (CAS No. 8007-02-1), with a light yellow color and a strong, sharp odor of fresh-grassy lemon type;

*Zanthoxylum armatum* oil, ZA oil (CAS No. 8015-91-6), with a yellow color;

*Hedychium spicatum* oil, HS oil (no CAS No. was found to be assigned as yet), with a greenish yellow color; and Menthol, M (CAS No. 2216-51-5) of USP grade and water-white crystal with its characteristic odor.

These oils and crystal were used without further purification, though their infra-red (IR) and nuclear magnetic resonance (NMR) spectra, and liquid chromatography (LC) traces were collected and archived for batch-to-batch data collection.

Blends of the above stated EOs were made for experimentation at various ratios; such blends were then picked up with a micropipette for emulsification for making creams.

Various other ingredients were procured for making water based cream preparations; for example, Deionized water, made at the lab premises via reverse osmosis method;

Preservatives: Gluconolactone and Sodium Benzoate, e.g. Geogard Ultra;

Thickener: Carbomer, e.g. Carbopol Ultrez-10;

Co-emulsifier: Glyceryl Stearate, e.g. Cutina GMSV;

Emulsifier: Cetearyl Alcohol and Steareth-30 and Ceteth-10, e.g. Phoenoxol T;

Solubilizer Propane Diol;

Solubilizer Glycerin;

Base (to assist in neutralization of the pH): Triethanolamine.

A cream formulation according to the present invention comprising the combination of 3 Essential oils as mentioned in Table 1 is prepared and the formulation of the same is provided in Table 1.

TABLE 1

Composition of the present formulation.

| Ingredient | Wt % |
|---|---|
| Phase-A | |
| Deionized Water | 76.2% |
| Gluconolactone and Sodium Benzoate - preservatives | 1.0% |
| Carbomer -thickener | 0.9% |
| Phase-B | |
| Glyceryl Stearate -co-emulsifier | 2.0% |
| Cetearyl Alcohol and Ceteth-20 and Steareth-10 Emulsifier | 3.0% |
| Essential Oil - 1 (e.g. CC Oil) | 3.0% |
| Essential Oil - 2 (e.g. HS Oil) | 1.0% |

TABLE 1-continued

Composition of the present formulation.

| Ingredient | Wt % |
|---|---|
| Essential Oil - 3 (e.g. ZA Oil) | 1.0% |
| Phase-C | |
| Propane Diol | 4.0% |
| Glycerin | 1.0% |
| Menthol | 1.0% |
| Phase-D | |
| Deionized Water | 5.0% |
| Triethanoiamine - Base | 0.9% |
| Total | 100.0% |

Example 2: Method for the Preparation of the Cream

The procedure for the preparation was as follows:

Step 1) Phase-A: Dispersing Carbopol in water, which is an acidic acrylic polymer. Then adding preservatives Gluconolactone and Sodium Benzoate, which are water-soluble. Heating the prepared mixture at 65 to 70° C. with mixing.

Step 2) Phase-B: Combining all the ingredients of Phase-B, and heating at 65 to 70° C. (This step has the EO's and the emulsifier mixed together the oils are added last when the temperature is reached so as to ensure minimum heating time for EOs.)

Step 3) Phase-C: Pre-mixing Phase-C in a separate vessel, and setting aside. (Menthol dissolves faster when warmed to 40° C.)

Step 4) Phase-D: Mixing Phase-D ingredients separately.

Step 5) Adding Phase-B to Phase-A at 65 to 70° C. with mixing at 400 to 500 rpm.

Step 6) Adding Phase-D to the blend of A and B, mixing and raising the speed to 900 rpm, as the emulsion thickens.

Step 7) Allowing the blend of ABD to cool to below 40° C. while mixing, and then adding Phase-C to ABD, and mixing.

Step 8) Cooling down the above blend of ABCD to room temperature with mixing and QS to 100 using DI-water. (QS means that you add DI-water such that the final weight is 100 g; it is assumed that the water phase evaporates partially during cream preparation.)

Example 3

The various properties of the above prepared cream of example 2 were studied.

A pH meter and a Brookfield viscometer were used for measuring pH and viscosity, respectively, of the cream prepared. The above resulted in a white cream of pH 5.5 and a viscosity of 180,000 cSt at 21° C.

Stability of the cream produced was evaluated after aging at 50° C. for four weeks in screw-cap glass containers. It gave a stable viscosity in the range of 150,000 to 200,000 cSt and a pH of about 5.0 to 5.1 at 21° C.

It was also observed that the cream was stable throughout five cycles of freeze-thaw, and it did not show changes in appearance or any sign of separation.

Example 4: Arthritic Mice Model and Treatment with Blends of EOs

Various samples of the neat blends of EOs were made as below with the above described procured EOs:

Example A: CC to ZA=6 to 4
Example B: CC to HS=6 to 4
Example C: CC to ZA to HS=6 to 2 to 2
Example D: Menthol was added in some of the cases at various ratios of CC to M, e.g. 100 to 1, 1 to 1, etc.

Such blends were then picked up with a micropipette for dispensing on collagen induced arthritic mice models for treatment at a droplet volume of 10 micro liters. These studies took around 3 weeks.

Arthritic Mice Model: Collagen induced arthritic mice model was developed in the laboratory by following the standard protocols published in the literature. (Julia Inglis et al have described this model in *Nature Protocols* 3, 612-618, 2008, "Protocol for the induction of arthritis in C57BL/6 mice". David Brand et al have described this in *Nature Protocols* 2, 1269-1275, 2007, "Collagen-induced arthritis".)

Type II collagen was dissolved in 10 mM acetic acid at a concentration of 3 mg/ml. 1 ml of Complete Freund's Adjuvant was mixed with 1 ml of the collagen-acetic acid solution. Then 50 micro liter of the solution was injected in the tail vein of the mice weighing 20 to 25 gm each. If required, a booster dose was injected after 21 days with the same dose and at the same site. Visual observation was made on the movement of the mice and video was taken at times. The mice clearly became arthritic, as evidenced by their slow movements, loss of cage riding ability and redness of paw. Blood samples were withdrawn before and after the mice became arthritic. These procedural steps may be summarized as shown in FIG. 1.

Treatment with EOs: The herbal EO's were then evaluated either as individual oils or as blends at certain ratios at a given dose. An aliquot of 10 micro liters of EO was collected with a micro pipette and applied on the thigh of the hind leg of the arthritic mice over an area of half inch by half inch approximately. After the drop was applied, a hair gun, used in drying wet hair, was used to volatilize any excess oil. This treatment continued daily for 20 days (no less than 20 days and no more than 25 days). At the end of the treatment period, blood sample was collected again. Data were collected at N=6 mice for each EO composition.

Blood samples were collected before and after the treatments with various EOs blends, and the serum was analyzed for cytokine levels using commercially available ELISA (Enzyme Linked Immuno-sorbent Assay) kits. These included TNF-alpha (TNF-α), Interleukin-1beta (IL-1b) and Interleukin-6 (IL-6). While various data were collected, representative sets are shown in Table 2 and FIGS. 2, 3 and 4. Also, note that the anti-inflammatory activity of the individual oils is known in the art as discussed in the background section of this specification, and the same is not re-performed, thus reducing the number of animal studied.

TABLE 2

ELISA Inflammatory Cytokines Study on Blood Serum in an Arthritic Mice Model with results before and after treatment of 21 days.

| Sample ID | Inflammatory Cytokines in Blood Serum of Mice (picogram per milligram protein) | | |
|---|---|---|---|
| | TNF-alpha | IL-6 | IL-1beta |
| Control (Healthy Mice) | 40 +/− 4 | 130 +/− 15 | 40 +/− 6 |
| Mice with Collagen Induced Arthritis, CIA | 140 +/− 12 | 300 +/− 35 | 100 +/− 12 |
| CIA + CC + ZA = CC/ZA at 60%/40% on CIA Mice | 90 +/− 15 | 205 +/− 17 | 70 +/− 7 |
| CIA + CC + HS = CC/HS at 60%/40% on CIA Mice | 85 +/− 13 | 210 +/− 20 | 65 +/− 7 |
| CIA + CC + ZA + HS = CC/ZA/HS at 60%/20%/20% on CIA Mice | 60 +/− 9 | 160 +/− 15 | 50 +/− 4 |

It is concluded that although it is known that CC oil shows a reduction in inflammatory cytokine levels, or that ZA oil and HS oil display a reduction in inflammatory cytokine levels, the results observed in Table 2 and FIGS. 2, 3 and 4 for the blend of CC oil, ZA oil and HS oil of the present invention composition were found to be unique, unexpected, and never reported earlier. While the weight proportions of CC oil and ZA oil, or CC oil and HS oil were held constant at 60% and 40% for the first oil and second oil respectively, it was clearly observed that the blend of CC oil, ZA oil and HS oil as comprised in the present composition demonstrated significant synergy in reducing the inflammatory cytokines. This was a consistent behavior in each of the cases of TNF-alpha (TNF-a), Interleukin-1beta (IL-1b) and Interleukin-6 (IL-6). Therefore, the blend CC oil, ZA oil and HS oil as comprised in the present composition is considered to have surprisingly beneficial anti-arthritic effects.

What is claimed:

1. A topical synergistic anti-inflammatory formulation comprising a blend of essential oils, wherein the blend includes at least three essential oils selected from:
   (A) *Cymbopogon citratus* oil (CC oil),
   (B) *Zanthoxylum armatum* oil (ZA oil),
   (C) *Hedychium spicatum* oil (HS oil), and
   (D) a fourth essential oil obtained from basil, caraway, carrot seed, celery seed, chamomile, citronella, clary sage, clove, cumin, lemon, marjoram, nutmeg, orange, sage, sandalwood, spearmint, and/or thyme.

2. The formulation of claim 1, wherein the blend includes:
   about 1 to about 6% by weight of the CC oil;
   about 0.5 to about 6% by weight of the ZA oil,
   about 0.5 to about 6% by weight the HS oil.

3. The formulation of claim 1, wherein the weight proportion of the CC oil, the ZA oil, the HS oil in the blend of essential oils is about 60%, about 20%, and about 20%, respectively.

4. The formulation of claim 1, wherein the total amount of the blend of essential oils is in the range from about 2 to about 16% by weight of the formulation.

5. The formulation of claim 1, wherein the formulation further comprises menthol.

6. The formulation of claim 5, wherein the formulation includes the menthol in an amount from about 1 to about 16% by weight of the formulation.

7. The formulation of claim 1, wherein said formulation is in a form of a cream, a gel, a lotion, or a spray.

8. The formulation of claim 1, wherein said formulation is in a form of an emulsion.

9. The formulation of claim 8, wherein said emulsion further comprises an emulsifier.

10. A method of management of pain and/or inflammation in a mammal in need thereof, said method comprising: administering the formulation of claim 1 at a site of the pain and/or inflammation.

11. The method as claimed in claim 10, wherein the formulation is configured to be topically applied.

12. The method of claim 10, wherein the blend includes:
about 1 to about 6% by weight of the CC oil;
about 0.5 to about 6% by weight of the ZA oil,
about 0.5 to about 6% by weight the HS oil.

13. The method of claim 10, wherein the weight proportion of the CC oil, the ZA oil, the HS oil in the blend of essential oils is about 60%, about 20%, and about 20%, respectively.

14. The method of claim 10, wherein the total amount of the blend of essential oils is in the range from about 2 to about 16% by weight of the formulation.

15. The method of claim 10, wherein the formulation further comprises menthol.

16. The method of claim 15, wherein the formulation includes the menthol in an amount from about 1 to about 16% by weight of the formulation.

17. The method of claim 10, wherein said formulation is in a form of a cream, a gel, a lotion, or a spray.

18. The method of claim 10, wherein said formulation is in a form of an emulsion.

19. The method of claim 18, wherein said emulsion further comprises an emulsifier.

\* \* \* \* \*